(12) United States Patent
Lyles

(10) Patent No.: US 7,641,898 B2
(45) Date of Patent: Jan. 5, 2010

(54) KERATINOCYTE-FIBROCYTE CONCOMITANT GRAFTING FOR WOUND HEALING

(75) Inventor: Mark B. Lyles, Great Lakes, IL (US)

(73) Assignee: Materials Evolution and Development USA, Inc., San Antonio, TX (US)

( * ) Notice: Subject to any disclaimer, the term of this patent is extended or adjusted under 35 U.S.C. 154(b) by 186 days.

(21) Appl. No.: 10/804,436

(22) Filed: Mar. 19, 2004

(65) Prior Publication Data

US 2004/0219133 A1 Nov. 4, 2004

Related U.S. Application Data

(60) Provisional application No. 60/456,723, filed on Mar. 21, 2003.

(51) Int. Cl.
*A01N 65/00* (2006.01)
(52) U.S. Cl. ..................................... 424/93.7
(58) Field of Classification Search ....................... None
See application file for complete search history.

(56) References Cited

U.S. PATENT DOCUMENTS

| 6,234,402 | B1 | 5/2001 | Ganan-Calvo | 239/8 |
| 6,479,052 | B1 * | 11/2002 | Marshall et al. | 424/93.7 |
| 6,497,875 | B1 * | 12/2002 | Sorrell et al. | 424/93.7 |

OTHER PUBLICATIONS

Cohen et al. Aerosolization of epidermal cells with fibrin glue for the epithelialization of porcine wounds with unfavourable topography, Plast. Reconstr. Surg., 2000, 107: 1208-1215, entire document.*
Watt F.M. Epidermal stem cells: markers, patterning and the control of stem cell fate, Phil. Trans. R. Soc. Lond. B, 1998, 353: 831-837, entire document.*
Arenholt-Bindslev, D. et al., *The Growth and Structure of Human Oral Keratinocytes in Culture*, J. Invest. Dermatology, vol. 88, No. 3, pp. 314-319, Mar. 1987.
Auchincloss, Jr., H., et al., *T-Cell Subsets, bm Mutants, and the Mechanisms of Allogenic Skin Graft Rejection*, Immunol Res 1989; 8:149-164, 1989.
Bertolami, D.D.S, D. Med. Sci., C. N. et al., *Preparation and Evaluation of a Nonproprietary Bilayer Skin Substitute*, Plastic and ReconstructiveSurgery, pp. 1089-1098, Jun. 1991.

Boyce, S. T., et al., *Structure of a collagen-GAG dermal skin substitute optimized for cultured human epidermal keratinocytes*, Journal of Biomedical Materials Research, vol. 22, pp. 939-957, 1988.
Boyce, S. T., et al.,*Skin Anatomy and Antigen Expression after Burn Wound Closure with Composite Grafts of Cultured Skin Cells and Biopolymers*, Anatomy and Antigens of Cultured Cells on Burns, vol. 91, No. 4, pp. 632-641, Jun. 1991.
Burke, M.D., J. F. et al., *Successful Use of a Physiologically Acceptable Artificial Skin in the Treatment of Extensive Burn Injury*, Artificial Skin and Burn Injury, vol. 194, No. 4, pp. 413-428, Apr. 1981.
Chvapil, M. *Considerations on manufacturing principles of a synthetic burn dressing: A review*, Journal of Biomedical Materials Research, Vo. 16, 245-263, 1982.
Desquenne Clark, L. et al., *A New Murine Model for Mammalian Wound Repair and Regeneration*, Clinical Immunology and Immunopathology, vol. 88, No. 1 pp. 35-45, Jul. 1998.
Cooper, M.D., M. L. et al., *Use of a composite skin graft composed of cultured human keratinocytes and fibroblasts and a collagen-GAG matrix to cover full-thickness wounds on athymic mice*, Surgery, vol. 109, No. 2, pp. 198-207, Feb. 1991.
Dogo, M.D., G., *Survival and Utilization of Cadaver Skin*, Plastic & Reconstructive Surgery, vol. 10, pp. 10-13, 1952.
Dellon, M.D., A. L., et al. *An Alternative to the Classical Nerve Graft for the Management of the Short Nerve Gap*, Plastic and Reconstructive Surgery, pp. 849-856, Nov. 1988.
Elliott, Jr., M.D., R. A., et al., *Use of Commercial Porcine Skin for Wound Dressings*, Biological Dressings, vol. 52, No. 4, pp. 401-405, Sep. 1972.
Fienberg, D.D.S., S. E., et al., *Healing of Traumatic Injuries*, Oral and Maxillofacial Trauma, pp. 13-57, 1991.
Fleischmajer, R., et al., *Immunochemistry of a Keratinocyte-Fibroblast Co-culture Model for Reconstruction of Human Skin*, The Journal of Histochemistry and Cytochemistry, vol. 41, No. 9, pp. 1359-1366, 1993.
Gallico, III, M.D., G. G., et al., *Medical Intelligence—Permanent Coverage of Large Burn Wounds with Autologous Cultured Human Epithelium*, New England Journal of Medicine, pp. 448-451, Aug. 1984.

(Continued)

*Primary Examiner*—Jon P Weber
*Assistant Examiner*—Satyendra K Singh
(74) *Attorney, Agent, or Firm*—King & Spalding L.L.P.

(57) ABSTRACT

A system and method for dispersing living cells onto an area of a subject lacking normal, healthy skin, such as an open wound surface, to form three dimensional epithelial tissue is provided. The cells are dispersed using an air-jet sprayer after being suspended in a soluble media such as dextran. The cells may be dispersed directly onto the area or onto a tissue scaffold or synthetic substance that promotes wound healing.

6 Claims, 1 Drawing Sheet

OTHER PUBLICATIONS

Green, H., et al., *Growth of cultured human epidermal cells into multiple epithelia suitable for grafting*, Cell Biology, vol. 76, No. 11, pp. 5665-5668, Nov. 1979.

Hefton, J. M., et al., *Guinea Pig Epidermal Cell Cultures: Development of Confluent Sheets and their Transplantation*, Federation Proceedings, vol. 39, No. 3, p. 736, Mar. 1980.

Hefton, J. M., et al., *Grafting of Burn Patients with Allografts of Cultured Epidermal Cells*, The Lancet, vol. II, No. 8347, pp. 428-430, Aug. 1983.

Hill, M. W., et al., *The influence of differing connective tissue substrates on the maintenance of adult stratified squamous epithelia*, Cell Tissue Research, 237, pp. 473-478, 1984.

Hill, M. W., et al., *The influence of subepithelial connective tissues on peithelial proliferation in the adult mouse*, Cell Tissue Research, 255, pp. 179-182, 1989.

Johnson, E. W., et al., *Serial Cultivation of Normal Human Keratinocytes: A Defined System for Studying the Regulation of Growth and Differentiation*, In Vitro Cellular & Developmental Biology, vol. 28A, No. 6, pp. 429-435, Jun. 1992.

Klebe, R. J., *Cytoscribing: A Method for Micropositioning Cells and the Construction of Two- and Three-Dimensional Synthetic Tissues*, Experimental Cell Research 179, pp. 362-373, 1988.

Klebe, R. J., et al., *Adhesive Substrates for Fibronectin*, Journal of Cellular Physiology 109, pp. 481-488, 1981.

Kohn, F. E., et al., *New perspectives in myringoplasty*, The International Journal of Artificial Organs, vol. 7, No. 3, pp. 151-162, 1984.

Krejci, N. C., et al., *In Vitro Reconstitution of Skin: Fibroblasts Facilitate Keratinocyte Growth and Differentiation on Acellular Reticular Dermis*, The Journal of Investigative Dermatology, pp. 843-848, 1991.

Leong, K. W., et al., *Bioerodible polyanhydrides as drug-carrier matrices. I: Characterization, degradation, and release characteristics*, Journal of Biomedical Materials Research, vol. 19, pp. 941-955, 1985.

Lynch, S. E., et al., *Growth Factors in Wound Healing—Single and Synergistic Effects on Partial Thickness Porcine Skin Wounds*, Journal of Clinical Investigation, vol. 84, pp. 640-646, Aug. 1989.

Mackenzie, I. C., et al., *In vitro reconstruction of compound canine mucosal tissues*, J. Dental. Res., 70: 438-448, 1991.

Milam, S.B., *An extracellular matrix graft which promotes bone healing by an osteoconductive mechanism*, University of Texas, S.A., Tx; pp. 103-134, 1990.

Morykwas, Ph.D., M. J., et al., *Scalp Necrosis in a Neonate Treated with Cultured Autologous Keratinocytes*, Plastic and Reconstructive Surgery, vol. 87, No. 3, pp. 549-552, Mar. 1991.

Murphy, G. F., et al., *Partial Dermal Regeneration is Induced by Biodegradable Collagen-Glycosaminoglycan Grafts*, Laboratory Investigation, vol. 63, No. 3, pp. 305-313, 1990.

O'Connor, N. E., et al., *Grafting of Burns with Cultured Epithelium Prepared from Autologous Epidermal Cells*, The Lancet, vol. I, No. 8211, pp. 75-78, Jan. 1981.

Parenteau, N. L., et al., *Epidermis Generated In Vitro: Practical Considerations and Applications*, Journal of Cellular Biochemistry, 45, pp. 245-251, 1991.

Park, G. B., *Burn Wound Coverings—A Review*, Biomat., Med., Dev., Art. Org., 6(1), 1-35, 1978.

Phillips, M.B., MRCP, T. J., et al., *Cultured Allogenci Keratinocyte Grafts in the Management of Wound Healing: Prognostic Factors*, J Dermatol Surg Oncol, 15:11, pp. 1169-1176, Nov. 1989.

Pittelkow, M.D., M. R., et al., *New Techniques for the In Vitro Culture of Human Skin Keratinocytes and Perspectives on Their Use for Grafting of Patients With Extensive Burns*, Mayo Clinic Proceedings, vol. 61, pp. 771-777, Oct. 1986.

Robinson, P. H., et al., *Patency and long-term biological fate of a two-ply biodegradable microarterial prosthesis in the rat*, British Journal of Plastic Surgery, 42, pp. 544-549, 1989.

Schmitz, D.D.S., J. P., et al., *The Critical Size Defect as an Experimental Model for Craniomandibulofacial Nonunions*, Clinical Orthopaedics and Related Research, No. 205, pp. 299-308, Apr. 1986.

Schmitz, J. P., et al., *Characterization of Rat Calvarial Nonunion Defects*, Acta Anatomica, 138/3/90, pp. 185-192, Jul. 1990.

Shakespeare, V. A., et al., *Growth of cultured human keratinocytes on fibrous dermal collagen: a scanning electron microscope study*, Burns, vol. 13, No. 5, pp. 343-348, 1987.

Shetty, BDS, V., et al., *Contribution of Normal and Abnormal Wound Healing to Complications*, Oral and Maxillofacial Surgery Clinics of North America, vol. 2, No. 3, pp. 463-469, Aug. 1990.

Sugihara, Hajme, et. al., *Reconstruction of the Skin in Three-Dimensional Collagen Gel Matrix Culture*, In Vitro Cellular & Developmental Biology, vol. 27A, No. 2, pp. 142-146, Feb. 1991.

Sumimoto, K. et al., *Application of a New Synthetic Absorbable Cuff Material to Vascular Anastomosis in Liver Grafting*, Transplantation—Brief Communications, vol. 46, No. 2, pp. 318-321, Jan. 1988.

Takagi, M.D., K. et al., *The Reaction of the Dura To Bone Morphogenic Protien (BMP) in Repair of Skull Defects*, Ann. Surg., vol. 196, No. 1, pp. 100-109, Jul. 1982.

Teepe, M.D., R. G. C., et al., *The Use of Cultured Autologous Epidermis in the Treatment of Extensive Burn Wounds*, The Journal of Trauma, vol. 30, No. 3, pp. 269-275, 1990.

Yannas, Ph.D., I. V., *What Criteria Should be Used for Designing Artificial Skin Replacements and How Well do the Current Grafting Materials Meet These Criteria*, The Journal of Trauma, vol. 24, No. 9, pp. S29-S39, Sep. 1984.

International Search Report and Written Opinion PCT/US2004/08622, 8 pages, Mailing Date Mar. 31, 2005.

* cited by examiner

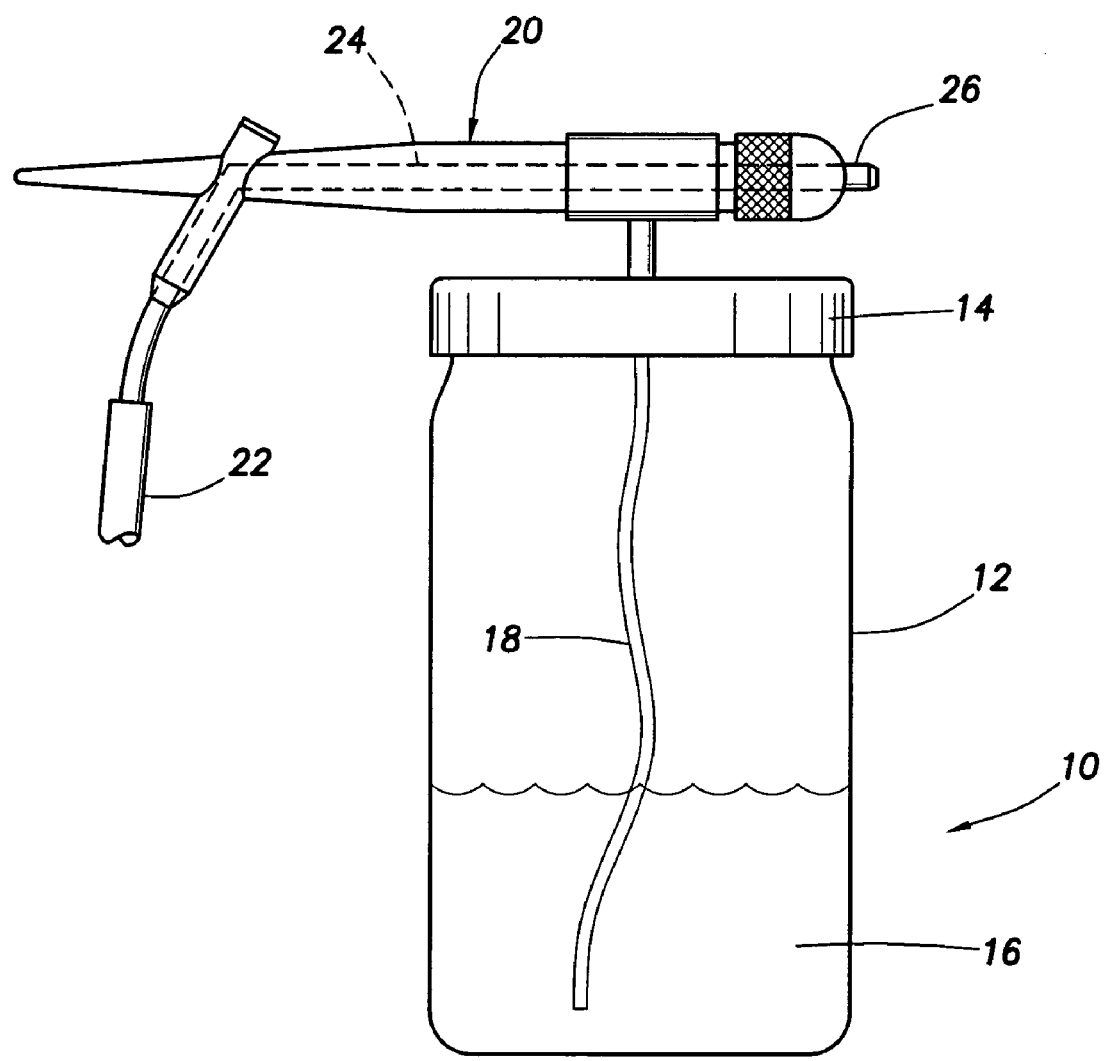

KERATINOCYTE-FIBROCYTE CONCOMITANT GRAFTING FOR WOUND HEALING

RELATED APPLICATION

This application claims priority to U.S. Provisional Patent Application Ser. No. 60/456,723, filed Mar. 21, 2003, and entitled Keratinocyte-fibrocyte Concomitant Grafting for Immediate Treatment of Severe Wounds: Use of an Air-jet Cell External Seeding Device (ACES).

TECHNICAL FIELD

The present invention relates to wound healing in general and specifically to a technique and system of seeding cells directly into a wound bed, for instance, using a handheld air-jet sprayer.

BACKGROUND OF THE INVENTION

Facilitation of the closure of large skin wounds (i.e. burns, traumatic injury, congenital reconstruction) by a variety of methods requires extensive expense and time. Methods currently in use include, but are not limited to, split-thickness grafts from the same individual, the use of specially treated cadaver skin, and autologous cultured skin equivalents. Due to the availability of these materials, it has become clinically feasible to treat skin wounds, particularly burn wounds, with cells cultured from the same patient. This method of treatment is both expensive and time consuming.

Although autologous grafting solves certain problems inherent in tissue transplantation, such as histocompatibility and the potential need for immunosuppressive agents, major problems still exist. For example, patients must not only suffer the harvesting of significant amounts of skin for autologous culturing, which in itself causes wounding, but must also wait up to six weeks before grafting back to the wound. For the patient, this is just the start of a long and trying process leading towards the healing of the wound.

The ability to treat skin wounds or congenital defects in which a significant amount of epithelial tissue has been lost or rendered nonfunctional remains an important issue among clinicians. With the advent of effective antibiotics, one major hurdle to effective wound healing, i.e. healing without infection, was effectively overcome. Thus, the use of antibiotics allowed for the routine use of surgical grafting techniques to be developed and applied to a wide range of wounds and defects. Recent history has seen the use of a variety of epithelial graft techniques which have contributed significantly to reducing the morbidity and mortality of individuals with severe skin wounds, including improved aesthetic results.

Clinical Aspects of Epithelial Grafts. Epithelial grafts fall into three main categories: allografts (same species), xenografts (different species), and autografts (same animal). Over the centuries xenografts from a variety of animals and birds have been used with wide ranging results. For the most part, little success was achieved with the use of different xenografts. The need for a viable alternative prompted the search for better graft material. Cadaver allografts are still in use today, but they are usually restricted to patients with extreme burns.

When available or practical, autografting from a healthy site on the individual to the wound site is the presently preferred treatment. This, however, may have some drawbacks. For instance, this leaves a donor site which must also be treated as a wound and can lead to increased morbidity of both the donor and graft sites. When only small amounts of tissue are used, free grafts may be transferred to sites that have an adequate blood supply and an intact and functional connective tissue base. For larger wound sites, pedicle grafts may be used. Pedicle grafts are initially allowed to remain attached to the donor site until an adequate collateral blood supply is developed before the connection to the donor site is excised.

For all of the previously described grafts, the success of the tissue graft is primarily dependent on: (a) immunological response to the graft; (b) size of the graft; (c) anatomical area of graft; (d) condition of underlying tissue at graft site; (e) condition of surrounding tissue at graft site; (f) thickness of graft; and (g) maintenance of sterility of graft tissue and graft site.

Cultured Epithelial Autografts. With advances in cell culture techniques came new ideas for tissue grafting. These advances in cell culture techniques have made it possible to culture keratinocytes (skin cells) taken from a biopsy of a patient and to ultimately transfer the resulting autologous cultured cells back to the same individual.

By using autologous cultured grafts, problems in organ transplantation procedures may be solved such as: (a) obtaining histocompatibility of matched tissues; and (b) lack of a graft donor site. In principle, this approach addresses many major problems of tissue transplantation. First, using the patient as their own source of transplant tissue, coupled with expansion of his/her cells in tissue culture, eliminates the problem of tissue availability in the majority of the patients who would benefit. Second, because a patient is treated with his/her own cells, an immunosuppressive mediator is not required, nor is there a requirement for a large donor site. This has opened up a new era in tissue transplantation, especially in the use of autologous cultured tissue grafts to treat severely burned patients. Yet, there are still some disadvantages, for example, the time and expense involved in culturing cells as well as the lack of available donor graft sites (e.g., burn patients with more than 60% tissue involvement). A need is recognized for a readily available source of graftable tissue which may be utilized in major trauma or burn cases.

Discussion of Epithelial Graft Construction. While the use of cultured cells in treatment of burns patients is now a routine clinical procedure, several problems remain to be solved. When epithelial cells are harvested from biopsy material, the cells that proliferate in culture are mainly connective tissue fibroblasts and keratinocytes. Sweat glands, sebaceous glands, pigment cells, and other cell types that are usually required for a fully functional skin are lost during cell cultivation and, as a result, cell culture derived autologous skin may lack several physiologically important properties.

The development of tissue engineered epithelial grafts for use in wound repair is an aggressively researched area. While the use of cultured cells in the treatment of burn patients is now an accepted clinical procedure several problems still remain to be solved. The time between the formation of the wound and the application of the graft material has a significant effect on scar formation and re-epithelialization. Using early culture techniques for the stratification of keratinocytes in vitro in the production of skin grafts, the stratification was limited to only a few cell layers without keratinization. Later techniques allowed further differentiation of the keratinocytes into a thicker stratified layer. Recently, keratinization of the cultured epithelial tissue was accomplished by growing confluent stratified cultures at the gas/liquid interface of the culture medium.

Because these tissues had minimum shear strength due to thickness (<0.5 mm), the grafting of such tissue required the use of a pressure bandage to hold the graft in place until a basement membrane had formed which attached the graft to the wound surface. These grafts were also limited by the type of wound, in that they were only useful as analogues of split-thickness autografts. Split-thickness grafts differ from full-thickness grafts in that the former contains little, if any, tissue below the basement membrane on which the epithelium attaches to the dermis. Therefore split-thickness autografts require grafting sites containing a healthy connective tissue layer. To date no such graft has ever formed secondary structural morphology such as rete ridges or appendageal structures. The lack of such structures makes the grafts highly sensitive to trauma and infection.

The reconstruction of full-thickness grafts from cultured cells has had limited success and, up until recently, only when autologous donor collagen was used. Recent reports using dermal allografts have had some success, such as the grafting of full-thickness cultured oral mucosal cells in the mouse and dog. This was accomplished by the construction of a bilayer graft containing autologous cultured keratinocytes grown directly on a collagen-gel interspersed with autologous cultured fibroblasts.

The two major drawbacks to this method have been: (a) the lack of secondary structural morphology (rete ridge formation); and (b) the latent shrinking of the grafted collagen layer. The latter complication has been the most difficult problem in the clinical use of autologous cultured synthetic grafts resulting in the occasional loss of the graft. Researchers have tried to overcome this hurdle by combining the advances in graft tissue design techniques with the use of a cross-linked collagen-GAG matrix and the use of dermal allografts. Preliminary reports using this technique have shown rudimentary rete ridge formation and a decrease in graft contracture.

Methods to combine the technology of tissue engineering with that of dermal allografts have as yet not been developed. Studies attempting to combine synthetic full-thickness grafts with that of biodegradable polymers and copolymers are in the early stages of development. However, there are many studies utilizing a variety of natural and synthetic materials for use as a matrix support substratum for tissue reconstruction and augmentation. The field of tissue engineering is rapidly gaining ground as an alternative to aggressive surgical techniques for the repair of wounds and other deformities.

SUMMARY OF THE INVENTION

The present invention relates to methods and systems for depositing cells to form new skin structures. The cells may be deposited in a wound bed or other area lacking normal, healthy skin.

In one embodiment, the cells deposited include autologous cells, such as keratinocytes, fibrocytes, stem cells. Cells may be deposited in layers of a single cell type or specific mixture of cell types.

Cells may be deposited in connection with other agents, such as allograft material placed in the wound bed, cytokines, adhesion molecules, and growth factors.

Deposition of cells according to the present invention may facilitate growth of skin or other three dimensional epithelial tissues. More specifically, it may facilitate wound healing.

Other methods of the invention relate to harvesting and growing autologous cells for later deposition using a hand help air-jet sprayer.

The use of a hand held-air jet sprayer may allow easy clinical use of some methods and systems of the present invention. Other methods and systems allow the direct transplant of autologous cells to a wound bed within a few days after wounding. In embodiments employing a dermal allograft as a basic substrate material onto which cells are sprayed, the allograft may facilitate cell growth and integration by providing an improved environment in which cells may grow.

BRIEF DESCRIPTION OF THE DRAWING

The following figure forms part of the present specification and is included to further demonstrate certain aspects of the present invention. The invention may be better understood by reference this drawing in combination with the description of embodiments presented herein.

FIG. 1 presents an isometric view of a hand held air-jet sprayer, according to an embodiment of the present invention.

DETAILED DESCRIPTION OF THE INVENTION

The present invention relates seeding of cells, such as autologous cells directly onto a wound or other area lacking normal, healthy skin with the use of a hand held air-jet sprayer.

In one embodiment the autologous cells may be transplanted back to the patient within hours to days following the formation of a wound by a variety of mechanisms.

In another embodiment of this invention a wound/graft model analog for in vitro study is provided.

To dispense multiple cell lines independently and efficiently, in certain embodiments a hand held air-jet sprayer may be used to deposit one or more different cell types (e.g., keratinocytes, fibrocytes, stem cells, etc.) directly onto a wound bed to facilitate cellular integration within the wound and to accelerate new epithelial growth as part of the wound healing process. In a more specific embodiment, live autologous cells, suspended in autologous serum, are sprayed using a "continuous" air-jet sprayer, directly onto a commercially available allograft placed within the wound bed.

Air-jet sprayers of the invention operate, in principle, like any common forced-air device. The sprayer uses the velocity of the air flowing through it to create a vacuum that pulls the cell containing media into the air flow resulting in an aerosol spray.

Referring now to FIG. 1, hand held air-jet sprayer 10, which represents one type of sprayer than may be used in the present invention, contains cells suspension 16 in container 12, which is then closed with cover 14. To spray cell suspension 16, air from air supply 22 moves through air channel 24 of sprayer tube 20 past the top of hose 18, drawing cell suspension 16 through hose 18 into sprayer tube 20 where it then exits through nozzle 26 as an aerosol spray.

The "air" in the air-jet sprayer may be a gas such as carbon dioxide, water vapor, oxygen, nitrogen, argon, helium, neon, or various combinations of any of those gases.

The air-jet nozzle, such as nozzle 26 in FIG. 1, may include various pore sizes or a range of pore sizes e.g. 50-100 micrometers, 100-500 micrometers, 500-1000 micrometers, 1000-2000 micrometers. In an exemplary embodiment the pore size of the air-jet nozzle is 1000 micrometers. Pore sizes may be chosen to be large enough to allow passage of cells during spraying without significant damage.

The cells may be suspended in a variety of soluble media including polyvinyl alcohol, albumin, dextrans, plasma, serum, other blood components, polymers of nucleic acids or combinations thereof. The soluble media may be at a temperature between 0° C. and 55° C. In another embodiment the soluble media may be between 34 and 40° C., for example 38° C.

Antibiotics or other drugs may also be dispensed using the air-jet sprayer with or without cells.

In another embodiment of the invention extracellular adhesion molecules, cytokines, and growth factors may be used to enhance the graft survival percentage and the rate of tissue differentiation. The rate and extent of graft differentiation, development, and cellular integration in this embodiment may be assessed using histological and immunohistochemical techniques. In a further embodiment of the invention in vitro models may be used to test multilayered/multicellular engineered tissues.

The following examples are included to demonstrate specific embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention.

EXAMPLES

Example 1

Air-Jet Cell External Seeding (ACES)

The invention may include a technique, termed Air-Jet Cell External Seeding (ACES), in which cells and/or adhesion proteins or growth factors may be seeded onto a dermal substrate by a hand held air-jet sprayer. In brief: (a) a commercially available hand held air-jet sprayer may be used to deposit cells which are suspended in autologous serum or other specified media; (b) the cells are seeded onto a commercially available dermal substrate (allograft) obtained from human cadaver skin; and (c) the construction of the resulting full thickness graft material can occur in vitro or in vivo.

This technology may utilize some techniques employed in a process known as cytoscribing which utilizes: (a) an ink cartridge of an inkjet printer filled with either fibronectin or other adhesion molecule; and (b) the deposition of the molecule on a substratum by a computer controlled printer. Subsequently, the cells only bind at sites where the adhesion molecule was applied.

Example 2

Harvesting and Culturing of Autologous Skin Graft Material in vitro

Engineered tissues of the present invention may contain keratinocytes and fibrocytes harvested from the same wound patient or from other sources. Specifically, keratinocytes may be obtained from a keratinized stratified epithelial surface which is unaffected by trauma or wounding, while fibrocytes may be obtained by liposuction. Keratinocytes may also be cultured from human neonatal foreskins. Fibrocytes may be obtained from adipose and dermal tissue via a tulip syringe during liposuction. Fibrocytes and undifferentiated adipocytes may be separated from the extracted adipose tissue along with collagen by enzymatic digestion and gentle agitation. Fibrocytes may also be obtained from human postpartum umbilical cord or neonatal foreskin dermis. The resultant fibrocytes or keratinocytes may be rinsed and concentrated prior to resuspension in autologous serum (or other media) and subsequent dispersion on the allograft matrix by air-jet spraying.

Example 3

Construction of in vitro Full Thickness Grafts

Dermal allograft material may be obtained from human cadavers. This dermal substitute consists primarily of collagen and may be used to construct an in vitro wound model analog by acting as an attachment matrix and in the orientation of a three-dimensional architecture for cell growth. This facilitates the in vitro study and development of clinical techniques in the construction of immediate autologous graft tissues. Autologous constructed tissues may be used in both transplantation studies and investigations into the cell biology of tissue engineering and wound healing.

ACES may be used to disperse and culture cells on the allograft substratum. Purified cell adhesion proteins and/or growth factors may be pre-incorporated into the allograft dermal matrix. Cell adhesion proteins (fibronectin, vitronectin, laminin, tenascin, fibrin) as well as growth factors (IGF, PDGF, TGF-$\beta$) may be used in tissue engineered autologous grafts.

Example 4

Animal Model Testing

The in vitro constructed synthetic tissue may be transferred to a surgically produced epithelial wound site on a recipient animal host. A critical size defect wound model similar in principle to that known utilizing the nude mouse may be used to test the effectiveness of autologous cultured synthetic tissues as graft materials. A critical size defect is a wound that is beyond a size to allow for normal healing usually resulting in the formation of a scar. In vitro cultured epithelial tissues may be grafted to full thickness epithelial wounds surgically created to mimic severe wound defects or third degree burns. The use of the nude mouse as a test animal offers two major advantages. One advantage is the lack of hair on the mouse which could ultimately restrict or inhibit graft suturing and bandage placement. The primary advantage of the nude mouse as a test animal is the ability to use xenogenic human cells in the production of in vitro cultured grafts.

Graft studies may be conducted in three stages. First, autologous constructed epithelium derived from keratinocytes and fibrocytes cultured on the allograft in vitro may be grafted to a surgically produced full-thickness wound consisting of an exposed subdermal layer. Second, immediate grafts produced in vitro over a 48 hr period using the ACES technique may also be transferred to the animal model. In the third stage, epithelial grafts may be constructed in vivo by surgically grafting the allograft material to the critical size epithelial wound site followed by the seeding of fibrocytes via air-jet spraying. This is followed by the in vivo seeding 24 hrs later of keratinocytes to the same wound bed and placement of dressings. Histological and immunohistochemical studies may be performed to evaluate the acceptance and incorporation of the graft during various stages of healing using a variety of techniques.

Studies with larger animals (i.e. pig) may use growth factors incorporated into either the autologous serum (or other suitable media) or the dermal allograft material prior to cell seeding. Autologous tissue engineered epithelial tissues may also be used in cleft lip/cleft palate repair, aesthetic scar removal, replacement of traumatically lost tissues and a variety of other potential surgical applications.

Example 5

New Methods to Harvest and Construct Three-dimensional Tissues in vitro.

Preparation of Fibrocytes. Fibroblasts may be primarily cultured from neonatal foreskin dermis in DMEM with 10% fetal bovine serum, 100 μg/ml ascorbic acid and antibiotics. Fibrocytes and undifferentiated adipocytes may be segregated from tissue obtained via liposuction. The extracted tissue may be washed and treated. The cells may be separated from the extracted tissue by gentle agitation in the presence of a sequential treatment of trypsin and collagenase as reporter.

Preparation of Keratinocytes. Cell cultures of skin epithelial cells may be prepared from tissue biopsy material, either neonatal foreskin or from blepharoplasty and/or rhytectomy procedures, using 0.125% trypsin (1:250) and 5 mM EDTA. Primary epithelial cell cultures may be grown in FAD medium with 3T3 feeder cells for 1-3 passages. These primary cultures may be grown at 33° C. to inhibit the growth of fibroblasts. The resulting keratinocytes may then be subcultured from single cell suspensions ($5 \times 10^6$ cells/ml) on a commercially available human dermal allograft substrate composed primarily of Type II collagen (AlloDerm, LifeCell Corporation, The Woodlands, Tex.). Stratification and differentiation of the squamous cell epithelium may be elicited using established methods utilizing Dulbecco's MEM with fetal bovine serum. After significant stratification with cultured epithelial cells, the resulting synthetic tissues may be raised on a grid to the gas/medium interface and incubated at 35° C. to induce epithelium organogenesis. Following amplification of the epithelial tissue mass during this last phase of cell culturing, the resulting composite graft tissue may be transplanted to the animal model.

Use of a universal dermal allograft. The universal dermal skin allograft (AlloDerm, LifeCell Corporation, The Woodlands, Tex.) is processed from human donor skin, which is used routinely as a temporary covering for extensive burns. Unprocessed human donor skin, however, is rejected in a matter of weeks. The tissue engineering process presently used in the field removes the epidermis, endothelial, and fibroblast cells from the donor skin which are targets for rejection, without altering the highly organized extracellular matrix. This dermal matrix is immunologically inert and, following grafting, becomes repopulated with the patient's own cells. These cells use the dermal template as a guide to remodel the missing skin.

Use of a new technique to deposit cells onto a commercially available dermal allograft. One may employ a hand held air-jet sprayer (Badger Model 900, Badger Air Sprayer Company, New York, N.Y.) to apply cells onto a substrate in vitro. A dermal allograft may be used as a matrix for cell deposition. For example, a universal dermal tissue graft processed from human donor skin (AlloDerm, LifeCell Corporation, The Woodlands, Tex.) may be used as the basic matrix material for cell growth. Both collagen and biodegradable plastics have been used for skin transplantation studies, however, the use of a dermal allograft is a superior substrata for constructing epithelial tissues for immediate grafting.

Quantity of cells deposited by the air-jet sprayer may be controlled by the concentration of cells per unit volume, by amount of eluent sprayed, and by the size of the droplet sprayed. The size of the droplet increases as the viscosity of the solution increases. The minimum concentration of cells sprayed is not normally less than $5 \times 10^6$ cells/ml for any cell type. Two different cell types, keratinocytes and fibrocytes, may be sprayed to produce a three-dimensional multicellular engineered tissue. Fibrocytes may be sprayed first onto the dermal allograft followed, after a set amount of time predetermined by experimental protocol, keratinocyte seeding. Existing cell culture technology and ACES, may be used to construct epithelial skin tissues suitable for grafting that contain both differentiated keratinocytes and fibrocytes.

ACES using live cells. The use of air-jet spraying is similar to the segregation of cells by fluorescence activated cell sorters (FACS). The principle technique used in FACS concerns only one nozzle that emits a continuous steam of charged droplets that are targeted by deflector plates. Thus, the technology involved in air-jet spraying is similar to that employed by fluorescence activated cell sorters, but differs in that the droplets are not charged and are considerably larger.

Preliminary studies have shown that it is possible to use live cells with a jet-air spray device. Initial studies indicate that one may deliver live mammalian cells to a substratum with a hand held air-jet sprayer. The problems of drying droplets and nozzle clogging have been largely overcome by the use of a larger nozzle orifice and by the possible addition of dextran to the cell suspended media. Dextran acts to "tie up" water thereby reducing the vapor pressure of water. The placing of wet dressings may alleviate the problem altogether. In vitro experiments take into account the use of a humidified $CO_2$ incubator and therefore drying is not a problem.

The nozzle orifice diameter used in the air-jet sprayer normally exceeds 1000 μm, and is therefore, in excess of the orifice diameters used in FACS or Coulter counters. Methods to deliver living cells to a substratum in vivo using a hand held jet-air sprayer device may be used as a very simple means of constructing tissue engineered skin in an very short time.

Evaluation of a dermal allograft for use with air-jet spraying devices. Commercially available dermal allograft material obtained from human cadavers may be used as a collagen matrix to construct three-dimensional skin grafts for animal transplantation studies. By utilizing primary cultures of fibrocytes and keratinocytes, a hand held air-jet sprayer may be used to deposit living cells onto a dermal allograft in vitro. Specifically a 2×1 cm piece of dermal allograft presoaked in fetal bovine serum (FBS) may be placed into polycarbonate petri dishes and allowed to sit for approximately two hours at 37° C. prior to ACES with fibrocytes. Immediately following seeding, the covered petri dishes may be placed back into a humidified $CO_2$ incubator at 37° C. and 10% $CO_2$.

Techniques for the immediate preparation of three-dimensional tissues in vivo. Three-dimensional tissue engineered grafts may be constructed in vivo, easily and efficiently, by using a hand held air-jet spraying device.

Such procedures may be carried out using a hand held air-jet sprayer technique, coupled with accelerated harvesting techniques. By using the ACES technique, it may be possible to construct epithelial tissues in vivo to immediately repair of large external full-thickness wounds. Multiple layers of the various cell types may be sprayed onto a collagen allograft by multiple passes using the ACES method to vary tissue thickness. The parameters of ACES methods to deposit live cells may be varied. Clinical methodologies may be used for the transplanting of autologous cultured cells and the construction and culturing of tissue engineered epithelial grafts.

Grafting procedure. Tissue engineered skin from in vitro cultured grafts (n=6), from immediate ACES prepared in vitro grafts (n=6), and from ACES prepared in vivo grafts (n=6), may be grafted. Controls, if used, may consist of surgical wounds without repair (n=6), wounds with only dermal allograft soaked in saline (n=6), wounds repaired with autologous serum soaked allograft (n=6), and wounds repaired with fibrocyte seeded allograft material. Nude mice (balb/c, nu/nu, NIH) may be anesthetized by intraperitoneal injection of ketamine and xylazene (Rumpun[8]) and a 2 cm longitudinal by a 1 cm vertical incision may be made through the skin and the panniculus carnosus (approximately 1-2 mm) on the lateral side of the back and flank. The tissue engineered grafts may be placed dermis side down and sutured into place prior to rinsing and dressing placement. The protocol for in vivo prepared immediate grafts may differ in that the fibrocytes may be sprayed directly onto the allograft just prior to suturing. Following the placement and suturing of the fibrocyte seeded dermal allograft, keratinocytes may be applied using the ACES technique. Approximately 30 minutes may be allowed for cell adhesion before the placement of the wound dressing.

Surgical Application, Dressing, and Wound Care. Sites to receive cultured grafts include the flank and back of the nude mouse. Wounds may be excised to viable tissue (fat or deep dermis), as described above, and soaked overnight in wet dressings with Sulfamylon (mafenice acetate) solution prior to placement of in vitro cultured composite grafts. Approximately 24 hrs following surgical wounding, the wound bed may be irrigated thoroughly with sterile saline, and the composite cultured grafts may be placed onto the wound beds and sutured into place with 4-0 fast adsorbing gut (FAG) suture. Grafts may then be covered with wet dressings consisting of fine mesh gauze, cotton gauze, and spandex stapled to the surrounding skin. Wet dressings may be irrigated with antimicrobial solutions administered at 2-hour intervals on a protocol of 0.5% Sulfamylon solution followed by two additions of double antibiotic (DAB; 40 µg/ml neomycin sulfate and 200 units/ml polymyxin B sulfate). Otherwise wet dressings may be changed each day for five consecutive days. Dry dressings placed on day 6 and 7 may consist of Xeroform gauze, cotton gauze bolster, and spandex. Dry dressings may be changed twice daily and may contain 3 parts bacitracin ointment plus 1% silver sulfadiazine cream. On day 8 only a simple gauze dressing may be placed daily containing the regiment of antibiotic ointments detailed above. Grafted wounds may be observed at each dressing change until day 8 and once daily until day 10. After re-epithelialization is completed, pressure garments may be applied to the graft sites.

Light and Transmission Electron Microscopy (LM and TEM). Biopsies (3 mm punch) may be taken at 14, 30, 60 and 90 days at the graft wound interface. Biopsies may be rinsed in saline, bisected and fixed in 2% glutaraldehyde and 2% paraformaldehyde in a 0.1M Na cacodylate buffer, pH 7.4, and subsequently processed by standard TEM methods.

Immunofluorescence Staining and Skin Antigens. Antibodies may be used to determine differentiation products of the epidermal layer, basal lamina, anchoring zone, dermis, and the remainder of the extracellular matrix. Specimens for immunostaining may be fixed in acetone for 4-6 hrs and directly embedded in paraffin. Four-micrometer sections may be placed on poly-L-lysine coated slides, baked at 56° C. for 1 hr, and deparaffinized with xylene and acetone. Mouse monoclonal anti-human Type III collagen antibodies (MAb) and mouse MAb of Type VI collagen may be used. Polyclonal rabbit and monoclonal mouse antibodies to Type I, IV, V collagen, decorin, laminin, nidogen, tenasin, fibronectin, elastin, vitronectin, fibrillin and osteonectin are commercially available and may also be used. Epithelial differentiation may be confirmed by the presence of K10-keratin, trichohyalin, and filaggrin antibodies.

Routine immunohistochemical techniques may be employed as follows: Slides may be: (1) deparaffinized (xylene×3, 10 minutes in each bath); (2) rehydrated by placing in baths of 100%, 95% and 70% ethanol (10 minutes each); (3) washed with phosphate buffered saline, pH 7.6 (PBS×3, 5 minutes each); (4) incubated with protein block (1% normal goat serum) for 20 minutes at room temperature (wash with PBS×3, 5 minutes each); (5) incubated with 3% hydrogen peroxide for 5 minutes to block indigenous peroxidase (wash with PBS×3, 5 minutes each); and (6) incubated with the primary antibody, for 90 to 120 minutes at room temperature (wash with PBS×3, 5 minutes each).

To label the antibody, Biogenex (San Ramon, Calif.) StrAviGen link and label (horseradish peroxidase) and the Biogenex DAB (diaminobenzedine) labeling kit, used according to manufacturers instructions, give consistently strong labeling with little or no background. The link is anti-IgG with an attached biotin. The label is an avidin-biotin complex with horseradish peroxidase. Both of these kits are available either ready to use or in bulk form. The bulk kit is used according to the dilution for Super Sensitive labeling. Mayer's hematoxylin (Sigma) is used for a counterstain.

Although the present invention and its advantages have been described in detail, it should be understood that various changes, substitutions and alternations can be made herein without departing from the spirit and scope of the invention as defined by the following claims.

The invention claimed is:

1. A method of dispersing living cells onto a wound area of skin of a subject comprising:
    forming a suspension including a subject's isolated autologous stem cells in a soluble medium;
    placing the suspension into a receptacle of an air-jet sprayer having a nozzle orifice with a pore size of at least 1000 microns; and
    dispersing the suspension onto the wound area of skin of the subject using the nozzle orifice of the air-jet sprayer;
    wherein the forming the suspension and dispersing steps occur after, but within one day of the formation of the wound area.

2. The method of claim 1, further comprising placing a dermal allograft into the wound area.

3. The method of claim 1, further comprising dispersing the cells onto a tissue scaffold located in the wound area.

4. The method of claim 1, wherein the wound area comprises a burn wound.

5. The method of claim 1, further dispersing at least one other type of autologous cell suspension, separately onto the wound area using the air-jet sprayer.

6. The method of claim 1, further comprising dispensing at least one of antibiotic, cytokine, adhesion factor, or growth factor onto the wound area using the air-jet sprayer.

* * * * *